United States Patent
Park et al.

(10) Patent No.: US 11,389,117 B2
(45) Date of Patent: Jul. 19, 2022

(54) APPARATUS, METHOD, AND PROGRAM FOR PREDICTING HYPOGLYCEMIA, AND APPARATUS, METHOD, AND PROGRAM FOR GENERATING HYPOGLYCEMIA PREDICTION MODEL

(71) Applicant: POSTECH ACADEMY-INDUSTRY FOUNDATION, Pohang-si (KR)

(72) Inventors: Sung Min Park, Pohang-si (KR); Won Ju Seo, Wanju-gun (KR); Seung Hyun Lee, Daegu (KR)

(73) Assignee: POSTECH ACADEMY-INDUSTRY FOUNDATION, Pohang-si (KR)

( * ) Notice: Subject to any disclaimer, the term of this patent is extended or adjusted under 35 U.S.C. 154(b) by 0 days.

(21) Appl. No.: 16/605,272

(22) PCT Filed: Aug. 20, 2018

(86) PCT No.: PCT/KR2018/009512
§ 371 (c)(1),
(2) Date: Oct. 15, 2019

(87) PCT Pub. No.: WO2019/039808
PCT Pub. Date: Feb. 28, 2019

(65) Prior Publication Data
US 2020/0170578 A1    Jun. 4, 2020

(30) Foreign Application Priority Data
Aug. 21, 2017   (KR) .................. 10-2017-0105570

(51) Int. Cl.
*A61B 5/145* (2006.01)
*A61B 5/00* (2006.01)
(Continued)

(52) U.S. Cl.
CPC ........ *A61B 5/7264* (2013.01); *A61B 5/14532* (2013.01); *A61B 5/4848* (2013.01);
(Continued)

(58) Field of Classification Search
CPC . A61B 5/7264; A61B 5/14532; A61B 5/4848; A61B 5/7275; G16H 10/40;
(Continued)

(56) References Cited

U.S. PATENT DOCUMENTS

2002/0106709 A1*  8/2002  Potts ................ A61B 5/14532
                                                                    435/14
2003/0235817 A1* 12/2003  Bartkowiak ....... A61B 5/14532
                                                                     435/5
(Continued)

FOREIGN PATENT DOCUMENTS

| JP | 2004-286452 | 10/2004 |
| JP | 2012-181804 | 9/2012 |

(Continued)

OTHER PUBLICATIONS

Jung, Miyeon et al. "Prediction of Daytime Hypoglycemic Events Using Continuous Glucose Monitoring Data and Classification Technique." arXiv: Machine Learning (2017): n. pag. 1-14 (Year: 2017).*

(Continued)

*Primary Examiner* — Navin Natnithithadha
(74) *Attorney, Agent, or Firm* — Lex IP Meister, PLLC

(57) ABSTRACT

An apparatus for predicting hypoglycemia according to an exemplary embodiment of the present disclosure is an apparatus for predicting hypoglycemia, which predicts the occurrence of postprandial hypoglycemia using blood glucose-related information, wherein the blood glucose-related information includes a blood glucose level at a reference time, a blood glucose change rate over a duration from a (Continued)

mealtime to a postprandial peak blood glucose level time, a blood glucose change rate over a duration from the postprandial peak blood glucose level time to the reference time, and a blood glucose change rate at the reference time.

11 Claims, 5 Drawing Sheets

(51) Int. Cl.
| | |
|---|---|
| *G16H 20/17* | (2018.01) |
| *G16H 10/40* | (2018.01) |
| *G16H 50/20* | (2018.01) |
| *A61M 5/142* | (2006.01) |
| *A61M 5/172* | (2006.01) |

(52) U.S. Cl.
CPC ............ *G16H 10/40* (2018.01); *G16H 20/17* (2018.01); *G16H 50/20* (2018.01); *A61M 5/142* (2013.01); *A61M 5/1723* (2013.01)

(58) Field of Classification Search
CPC ........ G16H 20/17; G16H 50/20; G16H 50/30; A61M 5/142; A61M 5/1723; A61M 5/14244; A61M 2005/14208; G06N 99/00; G06N 20/00
See application file for complete search history.

(56) References Cited

U.S. PATENT DOCUMENTS

| | | | | |
|---|---|---|---|---|
| 2007/0016449 | A1* | 1/2007 | Cohen | G16H 20/10 705/3 |
| 2014/0118166 | A1* | 5/2014 | Hampapuram | G16H 50/30 340/870.16 |
| 2015/0182115 | A1* | 7/2015 | DeHennis | A61B 5/1459 600/316 |
| 2015/0289821 | A1* | 10/2015 | Rack-Gomer | A61B 5/1118 600/365 |
| 2015/0289823 | A1* | 10/2015 | Rack-Gomer | A61B 5/743 600/365 |
| 2016/0324463 | A1* | 11/2016 | Simpson | A61B 5/0077 |
| 2017/0049961 | A1* | 2/2017 | Roy | A61M 5/1452 |
| 2017/0053552 | A1* | 2/2017 | Zhong | A61B 5/4848 |
| 2017/0311903 | A1* | 11/2017 | Davis | A61B 5/024 |
| 2017/0368258 | A1* | 12/2017 | Fleischer | A61B 5/0531 |
| 2018/0169332 | A1* | 6/2018 | Sadeghzadeh | A61M 5/145 |

FOREIGN PATENT DOCUMENTS

| | | |
|---|---|---|
| JP | 2015-142665 | 8/2015 |
| KR | 10-2012-0047841 | 5/2012 |

OTHER PUBLICATIONS

Schoenberger JL, Koh CK, Hor T, Baldwin D, Reddy A, Rondinelli-Hamilton L. Insulin in the medical management of postprandial hypoglycemia in a patient with type 2 diabetes after gastric bypass surgery. Case Rep Endocrinol. 2012 (Year: 2012).*

Jung, M., Lee, Y., Jin, S., & Park, S. (2017). Prediction of Daytime Hypoglycemic Events Using Continuous Glucose Monitoring Data and Classification Technique. arXiv: Machine Learning. (Year: 2017).*

Sudharsan, B., Peeples, M., & Shomali, M. (2014). Hypoglycemia Prediction Using Machine Learning Models for Patients With Type 2 Diabetes. Journal of Diabetes Science and Technology, 9(1), 86-90. https://doi.org/10.1177/1932296814554260 (Year: 2014).*

Jung, M. (2016). Toward designing mobile software to predict hypoglycemia for patients with diabetes. Proceedings of the International Conference on Mobile Software Engineering and Systems. Published. https://doi.org/10.1145/2897073.2897129 (Year: 2016).*

Plis, K., Bunescu, R.C., Marling, C.R., Shubrook, J.H., & Schwartz, F. (2014). A Machine Learning Approach to Predicting Blood Glucose Levels for Diabetes Management. AAAI Workshop: Modern Artificial Intelligence for Health Analytics. (Year: 2014).*

Marling, C.R., Xia, L., Bunescu, R.C., & Schwartz, F. (2016). Machine Learning Experiments with Noninvasive Sensors for Hypoglycemia Detection. (Year: 2016).*

Eljil, K. S., Qadah, G., & Pasquier, M. (2013). Predicting hypoglycemia in diabetic patients using data mining techniques. 2013 9th International Conference on Innovations in Information Technology (IIT). Published. https://doi.org/10.1109/innovations.2013.6544406 (Year: 2013).*

\* cited by examiner

[FIG. 1]
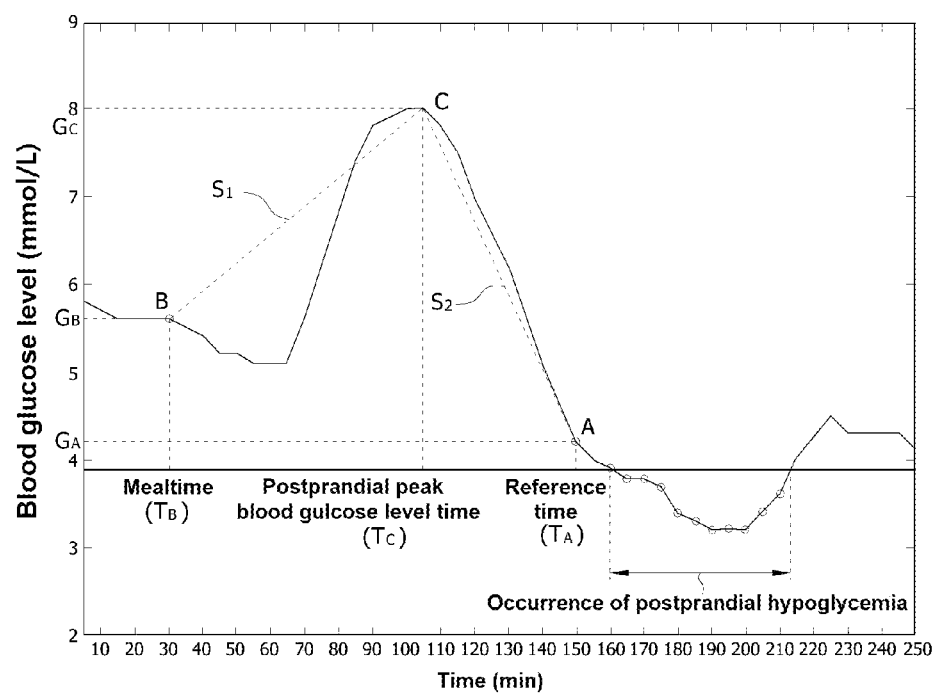

[FIG. 2]
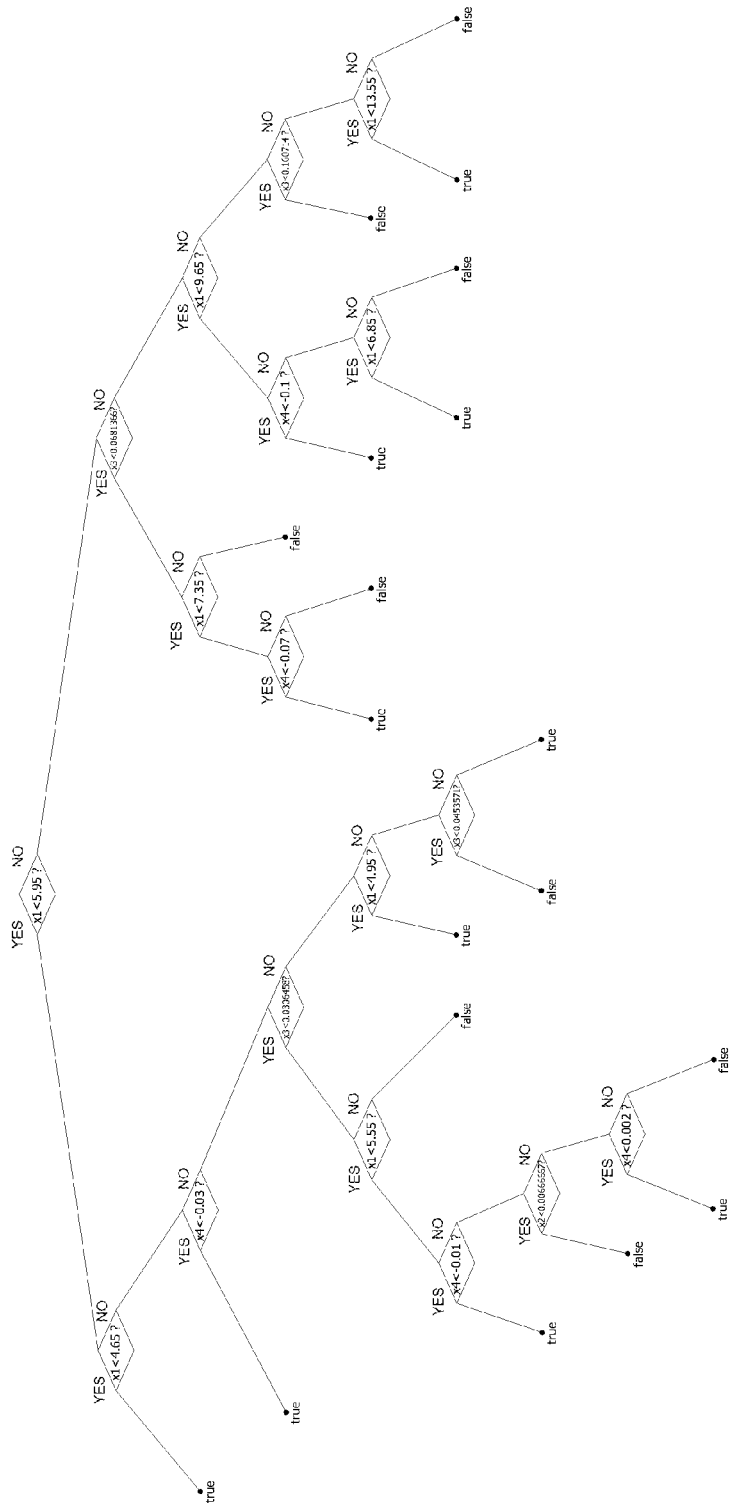

[FIG. 3]
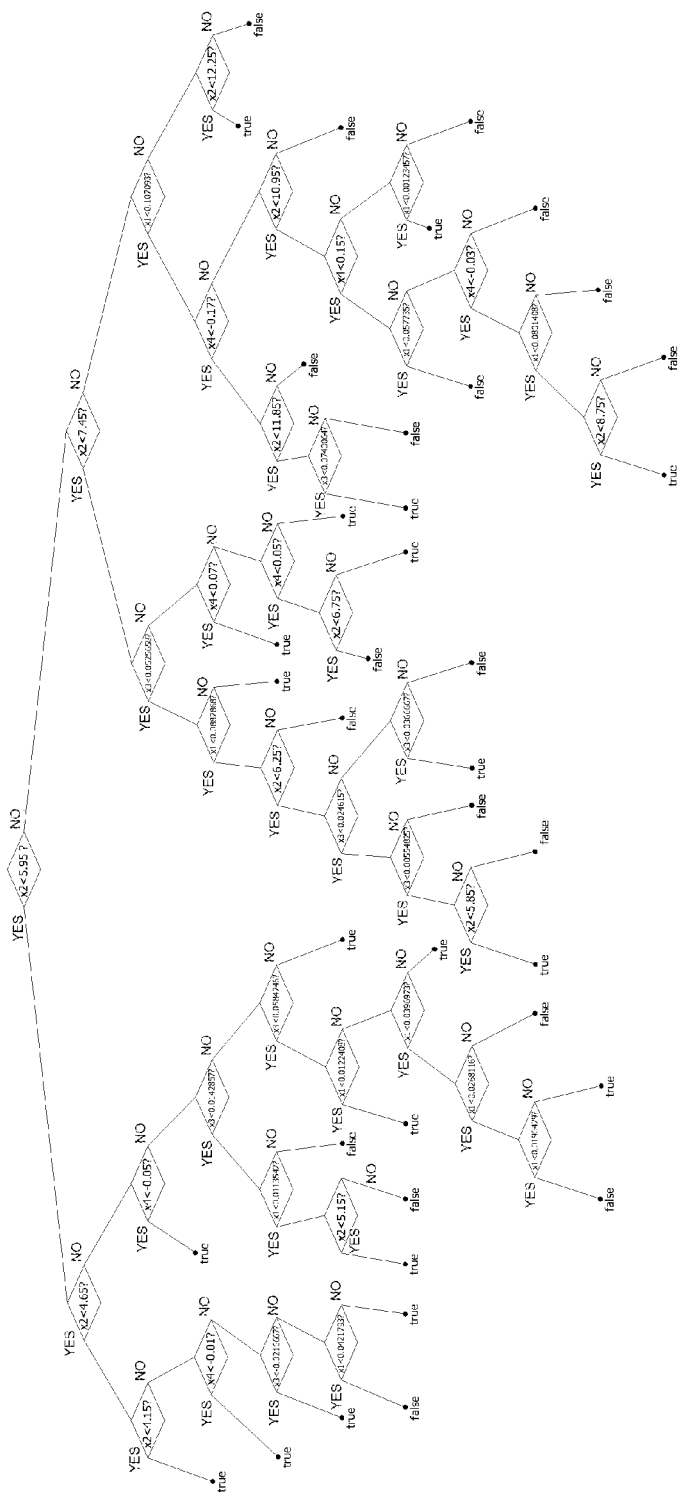

[FIG. 4]
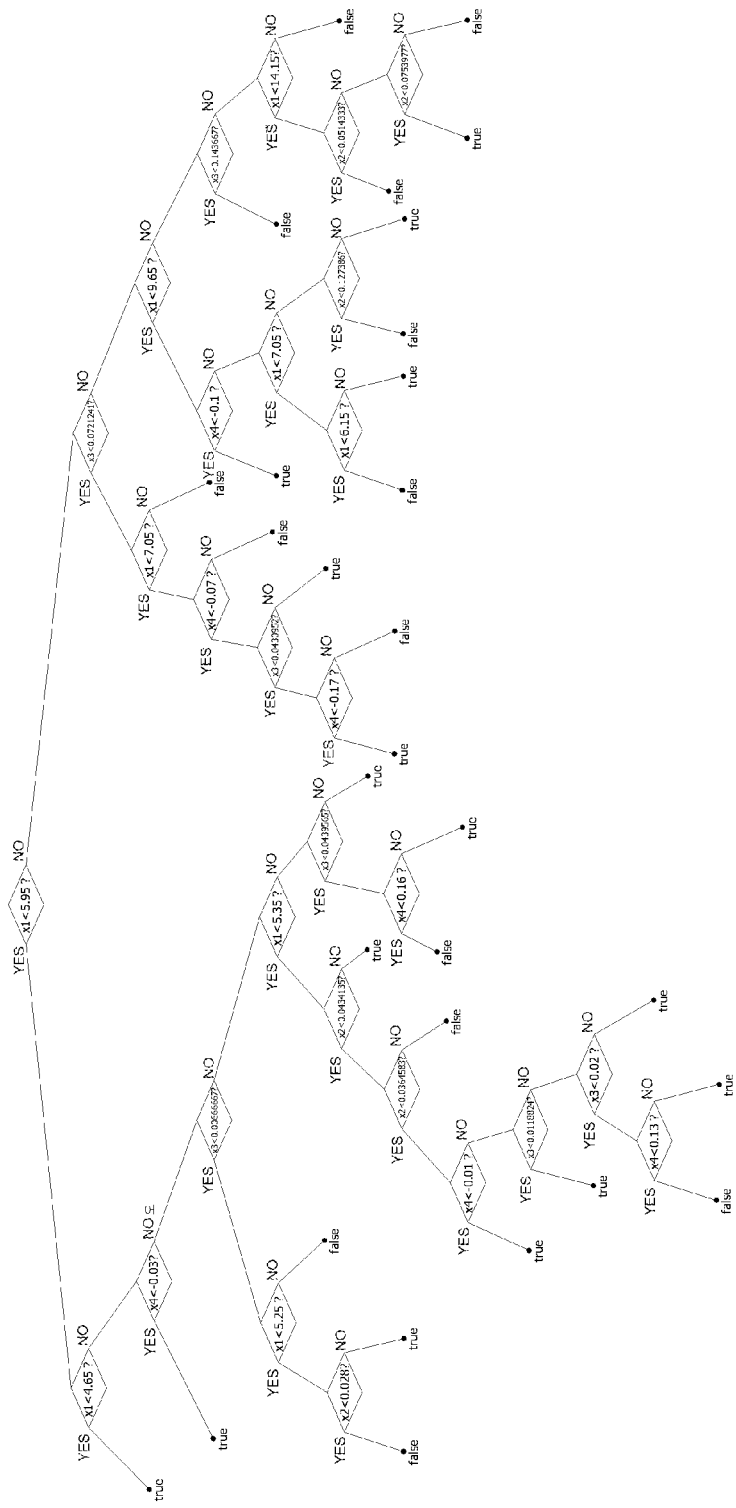

[FIG. 5]
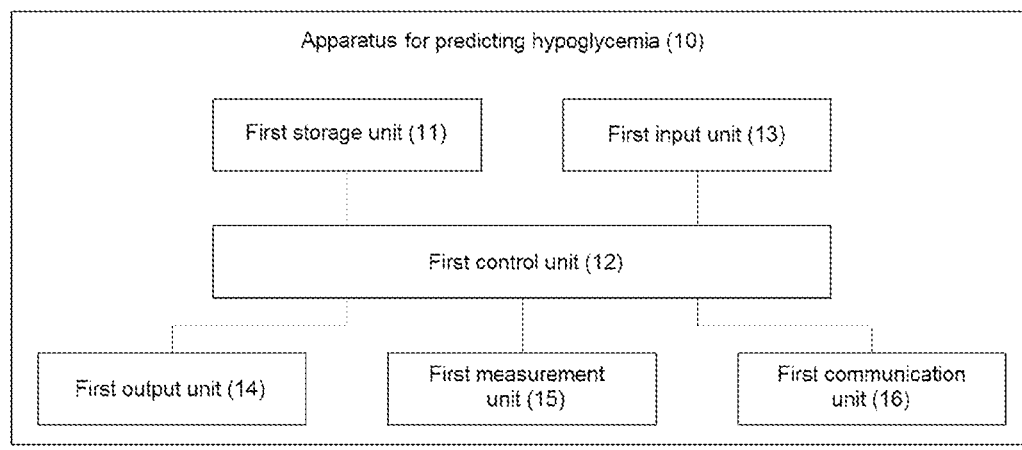
[FIG. 6]
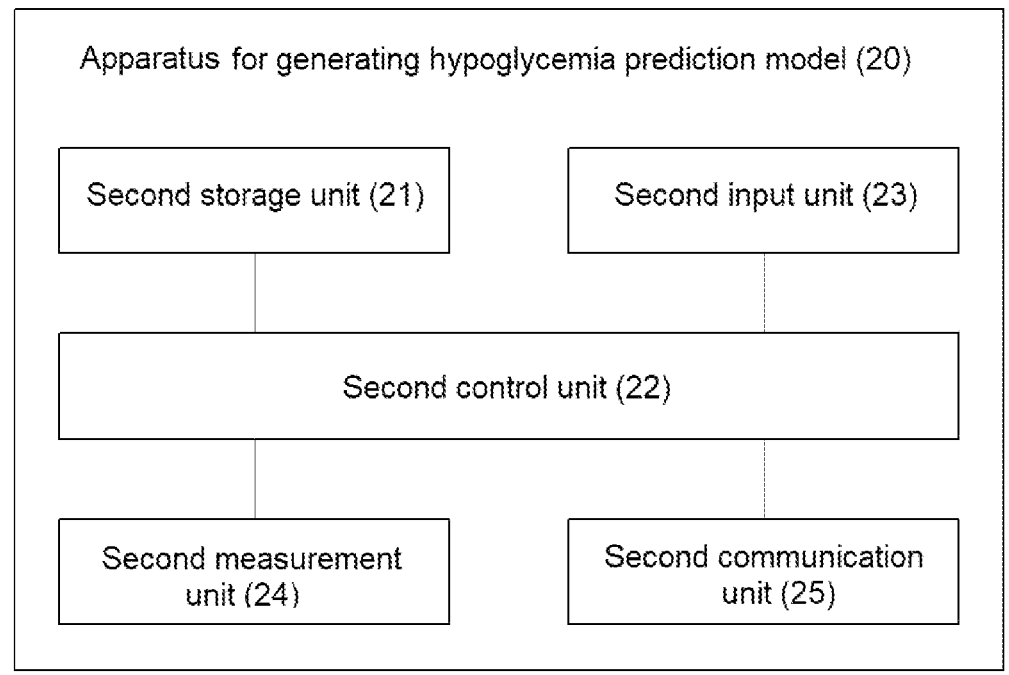

APPARATUS, METHOD, AND PROGRAM FOR PREDICTING HYPOGLYCEMIA, AND APPARATUS, METHOD, AND PROGRAM FOR GENERATING HYPOGLYCEMIA PREDICTION MODEL

TECHNICAL FIELD

The present disclosure relates to an apparatus, a method, and a program for predicting hypoglycemia, more particularly to an apparatus, a method, and a program for predicting hypoglycemia that may occur after a meal.

The present disclosure also relates to an apparatus, a method, and a program for generating a hypoglycemia prediction model, more particularly to an apparatus, a method, and a program for generating a model that predicts hypoglycemia that may occur after a meal.

BACKGROUND ART

Diabetes is a major disease suffered by 415 million people, which corresponds to 8.3% of the world population, as of 2015. The diabetes is classified into 'type 1 diabetes' where insulin is not secreted by the pancreas, and 'type 2 diabetes' where insulin is secreted from the pancreas but cannot be used effectively in the body.

Since diabetes is a metabolic disease where blood glucose is not controlled, blood glucose control is essential for patients with diabetes. If high blood glucose level is continued for a patient with diabetes because blood glucose is not controlled, severe complications such as stroke, retinopathy, nephropathy, neuropathy, diabetic foot, cardiovascular diseases, etc. may be caused.

Representative methods for treating diabetes and preventing its complications include medication of oral hypoglycemic agents or insulin infusion. However, these methods have problems in that precise blood glucose control is difficult and repeated medication or infusion with regular time intervals is inconvenient. To solve this problem, an insulin pump which automatically infuses insulin into the body has been developed. However, because the insulin pump infuses insulin intensively, there is another problem that hypoglycemia can be caused.

Hypoglycemia is a phenomenon accompanied by such symptoms as trembling, sweating, headache, etc. Continued hypoglycemia is dangerous because it can lead to hypoglycemic shock. Therefore, in order to prevent the occurrence of hypoglycemia in advance, a technology that can predict the occurrence of hypoglycemia symptoms in advance is needed.

The symptoms of hypoglycemia include 'nocturnal hypoglycemia' occurring in patients with diabetes during sleep and 'daytime hypoglycemia' occurring in patients with diabetes during activity.

The nocturnal hypoglycemia phenomenon is a phenomenon that occurs when the patient is sleeping at night. In other words, the nocturnal hypoglycemia phenomenon is a risky phenomenon which is difficult to cope with immediately because it occurs at night. However, because the nocturnal hypoglycemia phenomenon occurs when the patient with diabetes does not act, there are few factors that affect blood glucose change. Therefore, it is relatively easy to accurately predict the occurrence of the nocturnal hypoglycemia symptoms in advance. Currently, with the development of the technology capable of predicting the nocturnal hypoglycemia with high accuracy, it is being applied to an insulin pump, etc.

Meanwhile, the daytime hypoglycemia is a phenomenon that occurs when the patient with diabetes acts vigorously. That is to say, various factors affecting the change in blood glucose (e.g., stress, activity, food intake, etc.) are involved in the daytime and hypoglycemia phenomenon. Therefore, it is difficult to accurately predict the occurrence of daytime hypoglycemia in advance.

In particular, 'postprandial hypoglycemia' is a daytime hypoglycemia that occurs after a meal. In the past, postprandial hypoglycemia was predicted by considering various input information such as food intake, insulin infusion amount, etc. However, the existing postprandial hypoglycemia prediction technology is inconvenient in that the prediction accuracy may change due to incorrect input information (e.g., carbohydrate content in food) and various input information should be input by the patient with diabetes in a short period of time.

DISCLOSURE

Technical Problem

The present disclosure is directed to providing an apparatus, a method and a program for predicting hypoglycemia, which can conveniently predict the occurrence of postprandial hypoglycemia in advance with high accuracy.

The present disclosure is also directed to providing an apparatus, a method and a program for generating a hypoglycemia prediction model, which can predict the occurrence of postprandial hypoglycemia in advance conveniently with high accuracy.

Technical Solution

An apparatus for predicting hypoglycemia in accordance with an exemplary embodiment of the present disclosure is an apparatus for predicting hypoglycemia for predicting postprandial hypoglycemia using blood glucose-related information. Here, the blood glucose-related information includes blood glucose at a reference time, a blood glucose change rate from a mealtime to a postprandial peak blood glucose level time, a blood glucose change rate from the postprandial peak blood glucose level time to the reference time, and a blood glucose change rate at the reference time.

The apparatus for predicting hypoglycemia in accordance with an exemplary embodiment of the present disclosure can predict the occurrence of postprandial hypoglycemia due to insulin infusion or medication of oral hypoglycemic agents.

The apparatus for predicting hypoglycemia in accordance with an exemplary embodiment of the present disclosure can predict the occurrence of postprandial hypoglycemia by inputting the current blood glucose-related information to a previously stored machine learning model. Here, the machine learning model may be learned by using training data consisting of the previous blood glucose-related information and the occurrence of postprandial hypoglycemia.

The machine learning model may be a decision tree model or a deep learning model.

The machine learning model may be a decision tree model, and its root node can perform classification based on a predetermined value of the blood glucose at a reference time.

The decision tree model may include a plurality of first intermediate nodes, and any one of first intermediate nodes can perform classification based on a predetermined value of the blood glucose change rate from the postprandial peak blood glucose level time to the reference time.

The apparatus for predicting hypoglycemia according to an exemplary embodiment of the present disclosure can predict the occurrence of postprandial hypoglycemia in a predetermined time period after the reference time.

The apparatus for predicting hypoglycemia according to an exemplary embodiment of the present disclosure can generate blood glucose-related information by measuring and processing continuous blood glucose information, generate blood glucose-related information by processing continuous blood glucose information transmitted from another apparatus, or can receive blood glucose-related information from another apparatus.

The blood glucose-related information can be updated in real time.

The apparatus for predicting hypoglycemia in accordance with an exemplary embodiment of the present disclosure may be any one of an insulin pump, a continuous glucose monitor, a composite apparatus of an insulin pump and a continuous glucose monitor, an artificial pancreas apparatus, a wearable apparatus, and a hand-held apparatus.

The apparatus for predicting hypoglycemia according to an exemplary embodiment of the present disclosure can generate blood glucose-related information by processing continuous blood glucose information transmitted from another apparatus, or can receive blood glucose-related information from another apparatus. Here, the apparatus for predicting hypoglycemia in accordance with an exemplary embodiment of the present disclosure may be any one of an insulin pump, a wearable apparatus, and a hand-held apparatus.

The apparatus for predicting hypoglycemia in accordance with an exemplary embodiment of the present disclosure can generate blood glucose-related information by measuring and processing continuous blood glucose information. Here, the apparatus for predicting hypoglycemia in accordance with an exemplary embodiment of the present disclosure may be any one of a continuous glucose monitor, a composite apparatus of an insulin pump and a continuous glucose monitor, and an artificial pancreas apparatus.

A hypoglycemia prediction method according to an exemplary embodiment of the present disclosure includes a step of predicting the occurrence of postprandial hypoglycemia by the apparatus for predicting hypoglycemia using blood glucose-related information. Here, the blood glucose-related information includes blood glucose at a reference time, a blood glucose change rate from a mealtime to a postprandial peak blood glucose level time, a blood glucose change rate from the postprandial peak blood glucose level time to the reference time, and a blood glucose change rate at the reference time.

A hypoglycemia prediction method according to an exemplary embodiment of the present disclosure can predict the occurrence of postprandial hypoglycemia due to insulin infusion or medication of oral hypoglycemic agents.

The hypoglycemia prediction method according to an exemplary embodiment of the present disclosure may further include a step of predicting the occurrence of postprandial hypoglycemia by inputting the current blood glucose-related information to an apparatus for predicting hypoglycemia in which a machine learning model learned using training data consisting of the previous blood glucose-related information and the occurrence of postprandial hypoglycemia is stored.

A hypoglycemia prediction program according to an exemplary embodiment of the present disclosure is recorded in a medium to predict the occurrence of postprandial hypoglycemia according to the above-described hypoglycemia prediction method.

An apparatus for generating a hypoglycemia prediction model according to an exemplary embodiment of the present of the disclosure is an apparatus which generates a hypoglycemia prediction model predicting the occurrence of postprandial hypoglycemia by inputting the current blood glucose-related information. Here, the hypoglycemia prediction model is a machine learning model learned using training data consisting of the previous blood glucose-related information and the occurrence of postprandial hypoglycemia. In addition, the previous blood glucose-related information includes blood glucose at a reference time, a blood glucose change rate from a mealtime to a postprandial peak blood glucose level time, a blood glucose change rate from the postprandial peak blood glucose level time to the reference time, and a blood glucose change rate at the reference time.

The method for generating a hypoglycemia prediction model according to an exemplary embodiment of the present disclosure is a method for generating a hypoglycemia prediction model which predicts the occurrence of postprandial hypoglycemia by inputting the current blood glucose-related information, and includes a step of generating a machine learning model learned using training data consisting of the previous blood glucose-related information and the occurrence of postprandial hypoglycemia. Here, the previous blood glucose-related information includes blood glucose at a reference time, a blood glucose change rate from a mealtime to a postprandial peak blood glucose level time, a blood glucose change rate from the postprandial peak blood glucose level time to the reference time, and a blood glucose change rate at the reference time.

The program for generating a hypoglycemia prediction model according to an exemplary embodiment of the present disclosure is recorded in a medium to generate a model for predicting the occurrence of postprandial hypoglycemia according to the above-described method for generating a hypoglycemia prediction model.

Advantageous Effects

An apparatus, a method and a program for predicting hypoglycemia according to an exemplary embodiment of the present disclosure configured as described above can conveniently predict the occurrence of postprandial hypoglycemia in advance with high accuracy.

In addition, the apparatus, method and program for generating a hypoglycemia prediction model according to an exemplary embodiment of the present disclosure can conveniently generate a model that can predict the occurrence of postprandial hypoglycemia in advance with high accuracy.

BRIEF DESCRIPTION OF DRAWINGS

FIG. 1 is a graph showing blood glucose change before and after a meal.

FIG. 2 shows an optimum performance decision tree model selected in accordance with a first experiment of a hypoglycemia prediction method according to an exemplary embodiment of the present disclosure.

FIG. 3 shows an optimum performance decision tree model selected in accordance with a second experiment of a hypoglycemia prediction method according to an exemplary embodiment of the present disclosure.

FIG. 4 shows an optimum performance decision tree model selected in accordance with a third experiment of a hypoglycemia prediction method according to an exemplary embodiment of the present disclosure.

FIG. 5 shows a block diagram of an apparatus for predicting hypoglycemia 10 according to an exemplary embodiment of the present disclosure.

FIG. 6 shows a block diagram of an apparatus for generating a hypoglycemia prediction model 20 according to an exemplary embodiment of the present disclosure.

DETAILED DESCRIPTION OF MAIN ELEMENTS

| | |
|---|---|
| 10: apparatus for predicting hypoglycemia | |
| 11: first storage unit | 12: first control unit |
| 13: first input unit | 14: first output unit |
| 15: first measurement unit | 16: first communication unit |
| 20: apparatus for generating hypoglycemia prediction model | |
| 21: second storage unit | 22: second control unit |
| 23: second input unit | 24: second measurement unit |
| 25: second communication unit | |

[Best Mode]

The above-described object and means and the effect of the present disclosure will become more apparent through the following detailed description and the accompanying drawings. Accordingly, those of ordinary skill in the art to which the present disclosure belongs will be able to carry out the present disclosure easily. When describing the present disclosure, detailed description of the known art related with the present disclosure will be omitted if it is determined that it can unnecessarily obscure the subject matter of the present disclosure.

Also, the terms used in the present specification are for purposes of describing exemplary embodiments, and are not intended to limit the present disclosure. In the present specification, the singular expression shall include the plural expression as the case may be, unless otherwise noted in the text. The expression "includes (comprises)" and/or "including (comprising)" used in the specification does not preclude the presence or addition of one or more components other than the components mentioned. Unless otherwise defined, all terms used in the present specification will be used as the meanings that can be commonly understood by those of ordinary skill in the art to which the present disclosure belongs. And, the terms that are defined in general dictionaries should not to be construed as overly ideally or excessively unless otherwise defined.

In the present specification, the expression such as "or", "at least one", etc. may indicate one or a combination of two or more of the listed words. For example, "A or B" and "at least one of A and B" may include only one of A and B, and may also include both A and B.

Hereinafter, specific exemplary embodiments according to the present disclosure will be described in detail with reference to the accompanying drawings.

FIG. 1 is a graph showing blood glucose change before and after a meal.

A hypoglycemia prediction method according to an exemplary embodiment of the present disclosure is a method which predicts hypoglycemia that may occur after a meal using 'blood glucose-related information'. It can be performed by an apparatus for predicting hypoglycemia. Hereinafter, the hypoglycemia occurring after a meal will be referred to as "postprandial hypoglycemia".

The blood glucose-related information may be generated by processing continuous blood glucose information. The continuous blood glucose information is information about the blood glucose level of a subject measured continuously for a predetermined period of time (e.g., from a mealtime to a reference time). The 'continuous measurement' includes measurement at predetermined time intervals (e.g., any of 1 second to 10 minutes) or at every irregular time intervals.

That is, the continuous blood glucose information includes a plurality of pieces of blood glucose information. Here, each blood glucose information includes information about "measurement time" and information about "the blood glucose level of a subject measured at each measurement time". For example, the continuous blood glucose information may include n pieces of blood glucose information (where, n is a natural number which is 2 or greater). Here, the first blood glucose information is blood glucose information at the first time, and the n-th blood glucose information is blood glucose information at the reference time.

Specifically, the blood glucose-related information includes ①"blood glucose at a reference time", ②"a blood glucose change rate from a mealtime to a postprandial peak blood glucose level time", ③"a blood glucose change rate from the postprandial peak blood glucose level time to the reference time", and ④"a blood glucose change rate at the reference time".

The "blood glucose at a reference time" ($G_A$) refers to the blood glucose level of a subject measured at the reference time ($T_A$). Here, the 'reference time' is the time associated with the generation of the blood glucose-related information. That is to say, the reference time at which the blood glucose-related information is generated on the current time (hereinafter referred to as "the current blood glucose-related information") means the current time. And, the reference time at which the blood glucose-related information is generated on the past time (hereinafter referred to as "the previous blood glucose-related information") means the past time. However, the "current time" may also include time within a certain range from the precise current time. And, the "past time" may also include time within a certain range from the precise past time.

Meanwhile, the "blood glucose at the reference time" may correspond to the information for considering the blood glucose change at the reference time. Further, the "blood glucose at the reference time" may correspond to the information that can be used as a prediction reference point of occurrence of postprandial hypoglycemia. Thus, the "blood glucose at the reference time" may be reflected in a root node of a decision tree model which will be described later.

The "blood glucose change rate ($S_1$) from the mealtime ($T_B$) to the postprandial peak blood glucose level time ($T_C$)" is the change rate between the "blood glucose level of a subject measured at a mealtime" ($G_B$) and the "maximum of the blood glucose level of the subject measured after the mealtime" ($G_C$) (hereinafter, referred to as a "peak postprandial blood glucose level") ($[G_C-G_B]/[T_C-T_B]$). That is, the "blood glucose change rate from the mealtime to the postprandial peak blood glucose level time" may correspond to information for considering the rapid rise of blood glucose level that can occur after a meal. However, the 'mealtime' may include a predetermined time range around the precise mealtime. In addition, the 'mealtime' may be determined by a user input or may be derived from the trend of glucose level. And, the 'peak postprandial blood glucose level time' may include a predetermined time range from the precise time of the maximum postprandial blood glucose level.

The "blood glucose change rate ($S_2$) from the postprandial peak blood glucose level time ($T_C$) to the reference time ($T_A$)" is the change rate between the "postprandial peak blood glucose level" ($G_C$) and the "blood glucose level of the subject measured at the reference time" ($G_A$) ([$G_C$-$G_A$]/[$T_A$-$T_C$]). That is, the "blood glucose change rate from the postprandial peak blood glucose level time to the reference time" may correspond to information for considering the decrease of blood glucose level that can occur following the postprandial peak blood glucose level.

The "blood glucose change rate at the reference time" is a change rate between the "blood glucose level of the subject measured at a time ahead of the reference time by a first time" and the "blood glucose level of the subject measured at the reference time". That is, the "blood glucose change rate at the reference time" may correspond to information for considering the blood glucose change at the reference time. After a long time has passed after a meal, the "blood glucose change rate from the postprandial peak blood glucose level time to the reference time" does not change a lot. Accordingly, the "blood glucose change rate at the reference time" may correspond to information for compensating for the "blood glucose change rate from the postprandial peak blood glucose level time to the reference time" which does not change significantly.

Here, the 'first time' is the time interval for which the instantaneous blood glucose change rate at the reference time can be obtained. Therefore, the value of the first time is smaller than the difference between the reference time and the peak postprandial blood glucose level time. For example, the value of the first time may be the difference between the measurement times of the n-th blood glucose information (the blood glucose information at the reference time) and the (n-1)-th blood glucose information (the blood glucose information at the immediately before the reference time). That is to say, the first time may be from 1 second to 10 minutes, although not being limited thereto.

There may be a technology of predicting the occurrence of hypoglycemia using the "blood glucose at a reference time" and the "blood glucose change rate at the reference time" only (hereinafter referred to as "another prediction technology"). However, because the another prediction technology predicts the occurrence of hypoglycemia using only the two factors, it cannot reflect the rapid blood glucose change occurring after a meal. Thus, when the occurrence of postprandial hypoglycemia is predicted by the another prediction technology, the accuracy of prediction may decrease. Experiments for predicting the occurrence of hypoglycemia using the "blood glucose at a reference time" and the "blood glucose change rate at the reference time" only (first comparative experiment and second comparative experiment) and the result thereof will be described later.

The hypoglycemia prediction method according to an exemplary embodiment of the present disclosure predicts the occurrence of hypoglycemia using, in addition to the "blood glucose at the reference time" and the "blood glucose change rate at the reference time", the factors reflecting the rapid blood glucose change occurring after a meal. That is, the "blood glucose change rate from the mealtime to the postprandial peak blood glucose level time" and the "blood glucose change rate from the postprandial peak blood glucose level time to the reference time" may reflect the rapid blood glucose change occurring after a meal. Therefore, the hypoglycemia prediction method according to an exemplary embodiment of the present disclosure is advantageous in that the occurrence of postprandial hypoglycemia can be predicted with high accuracy.

The occurrence of postprandial hypoglycemia can be influenced by insulin or oral hypoglycemic agents infused or taken in at a mealtime or the amount of food intake. Here, the "mealtime" means any time from a predetermined time prior to a meal to a predetermined time after the meal. For example, the "mealtime" may be any time from 30 minutes prior to a meal to 15 minutes after the meal, although not being limited thereto.

However, the another prediction technology does not reflect the effect of insulin infusion or medication of oral hypoglycemic agents food intake. Thus, the another prediction technology cannot predict postprandial hypoglycemia which may occur when the peak blood glucose level is late or lower than expected after insulin infusion or medication of oral hypoglycemic agents during the mealtime, or when the amount of insulin infusion or medication of oral hypoglycemic agents is larger than the calculated amount of food intake.

In contrast, the "blood glucose change rate from a mealtime to a postprandial peak blood glucose level time" and the "blood glucose change rate from the postprandial peak blood glucose level time to the reference time" are the factors that reflect the rapid blood glucose change after food intake and may reflect not only the rapid blood glucose change due to food intake but also the effect due to insulin infusion or medication of oral hypoglycemic agents.

In particular, the "blood glucose change rate from the mealtime to the postprandial peak blood glucose level time" may reflect the increased possibility of postprandial hypoglycemia that may occur due to insulin infusion or medication of oral hypoglycemic agents owing to a low peak blood glucose level because the amount of food intake is low or the portion of carbohydrates in the meal is low. In addition, the "blood glucose change rate from the mealtime to the postprandial peak blood glucose level time" may reflect the phenomenon that the possibility of hypoglycemia due to infusion or medication of oral hypoglycemic agents increases as the blood glucose level falls sharply after the peak blood glucose level. Therefore, the hypoglycemia prediction method according to an exemplary embodiment of the present disclosure is advantageous in that the occurrence of postprandial hypoglycemia due to 'insulin infusion' or 'medication of oral hypoglycemic agents' can be predicted with high accuracy.

The hypoglycemia prediction method according to an exemplary embodiment of the present disclosure can continuously generate blood glucose-related information in real time from after food intake. Accordingly, the hypoglycemia prediction method according to an exemplary embodiment of the present disclosure can predict the occurrence of postprandial hypoglycemia in real time continuously from after a meal using the generated blood glucose-related information. However, the "continuous prediction of postprandial hypoglycemia in real time" includes prediction of the occurrence of postprandial hypoglycemia at predetermined time intervals (e.g., from 1 second to 10 minutes) or at irregular time intervals.

The postprandial hypoglycemia occur not immediately after a meal but after a certain period of time from a meal (e.g., 30 minutes after a meal). Once postprandial hypoglycemia occurs, a sequela may remain after it is treated, and a certain amount of time is needed to raise the blood glucose level. Therefore, if the occurrence of postprandial hypoglycemia is predicted, measures should be taken in advance before the postprandial hypoglycemia occurs. Furthermore, once the hypoglycemia occurs, it is continued for a certain period of time (e.g., at least 15 minutes).

Thus, the hypoglycemia prediction method according to the present disclosure can predict the occurrence of postprandial hypoglycemia within a predetermined time period after the reference time by reflecting the characteristic phenomenon of hypoglycemia, where postprandial hypoglycemia occurs after a certain period of time after a meal, and the postprandial hypoglycemia should be prevented before the postprandial hypoglycemia occurs, and the postprandial hypoglycemia is continued for a certain period of time.

For example, the hypoglycemia prediction method according to an exemplary embodiment of the present disclosure can predict the occurrence of postprandial hypoglycemia between 30 and 45 minutes after the reference time. In this case, the occurrence of postprandial hypoglycemia is predicted continuously in real time between 30 and 45 minutes after a meal. Accordingly, once the occurrence of postprandial hypoglycemia is predicted, at least about 30 minutes of time can be ensured to deal with it. Since enough time is given as such, the hypoglycemia prediction method according to an exemplary embodiment of the present disclosure is advantageous in that the occurrence of postprandial hypoglycemia and the sequela thereof can be prevented in advance. If hypoglycemia occurs, the hypoglycemia phenomenon is overcome by eating a glucose candy or drinking a drink that increases blood glucose level within several minutes. Therefore, 30 minutes is enough for preventing the hypoglycemia phenomenon in advance by increasing blood glucose level. Moreover, it is advantages in that, by predicting postprandial hypoglycemia between 30 and 45 minutes, the prediction of postprandial hypoglycemia which lasts for at least 15 minutes once it occurs can be increased up to 45 minutes.

However, the "certain period of time after the reference time" being 30-45 minutes is only one example, and the hypoglycemia prediction method according to an exemplary embodiment of the present disclosure is not limited thereto.

In particular, the hypoglycemia prediction method according to an exemplary embodiment of the present disclosure can predict the occurrence of postprandial hypoglycemia using a machine learning model (hereinafter referred to as "hypoglycemia prediction model"). Here, the hypoglycemia prediction model is a model learned by a machine learning technique using training data consisting of the previous blood glucose-related information (input value or observation value) and the occurrence of postprandial hypoglycemia (output value or target value).

That is, the hypoglycemia prediction method according to an embodiment of the present disclosure can predict the occurrence of postprandial hypoglycemia by inputting the current blood glucose-related information to the hypoglycemia prediction model learned using the training data. For example, the hypoglycemia prediction model may be a decision tree model using a decision tree technique or a deep learning model using a deep learning technique, although not being limited thereto.

Hereinafter, exemplary embodiments for embodying the hypoglycemia prediction model will be described in more detail.

First, the embodying of a decision tree model as the hypoglycemia prediction model will be described. If the hypoglycemia prediction model is embodied as a decision tree model, it is advantageous in that high-speed calculation is possible because a smaller amount of calculation is required for the prediction of postprandial hypoglycemia and the occurrence of postprandial hypoglycemia can be predicted with a simple apparatus.

Specifically, a process for embodying the decision tree model can include first to third processes as described below.

1) First Process of Embodying decision Tree Model: Collection of Experimental Data The first process of embodying a decision tree model is a process of collecting experimental data. In other words, in order to embody a decision tree model, first training data and test data should be collected first. Here, the training data are data that used as learning data in a decision tree technique to create the decision tree model, and the test data are data used to test the performance of the decision tree model learned through the learning data. Hereinafter, the training data and the test data are collectively referred to as "experimental data".

The experimental data include the previous blood glucose-related information and the information about the occurrence of postprandial hypoglycemia as a single data set, and includes a plurality of data sets. The information about the occurrence of postprandial hypoglycemia is information about whether a subject associated with the previous blood glucose-related information has actually experienced postprandial hypoglycemia since the past time.

In particular, in order to reflect the fact that postprandial hypoglycemia occurs after a period of time from a meal and the postprandial hypoglycemia must be prevented in advance before the postprandial hypoglycemia occurs, it may be in the information about whether postprandial hypoglycemia has actually occurred within a certain period of time after the corresponding past time (e.g., 30-45 minutes).

2) Second Process of Embodying Decision Tree Model: Generation of Decision Tree Model The second process of embodying a decision tree model is a process of generating a decision tree model. That is, the experimental data collected after the first process of embodying a decision tree model are identified as training data and other data are identified as test data. Then, a decision tree model associating an input value (or observation value) and an output value (or target value) is generated through learning using the identified training data as learning data. Here, among the training data, the previous blood glucose-related information corresponds to the input value and the information about the occurrence of postprandial hypoglycemia corresponds to the output value. For example, ID3 (Iterative Dichotomiser 3), C4.5 (successor of ID3), C5.0 (successor of ID4), CART (Classification And Regression Tree), CHAID (CHi-squared Automatic Interaction Detector), MARS (Multivariate adaptive regression splines), etc. may be used as a decision tree algorithm, although not being limited thereto.

Due to the characteristics of the experiment, the number of the data for the occurrence of postprandial hypoglycemia is inevitably smaller than the number of the data for which postprandial hypoglycemia has not occurred. Accordingly, a decision tree model may be generated by reflecting the number of the data for which postprandial hypoglycemia has not occurred, whose number is relative smaller. For example, weights may be given to reflect the number of occurrence and non-occurrence of postprandial hypoglycemia, or the test data may be processed such that the number data for which the postprandial hypoglycemia has occurred can be oversampled, although not being limited thereto.

3) Third Process of Embodying Decision Tree Model: Performance Test for Decision Tree Model The third process of embodying a decision tree model is a process of performing a performance test for the generated decision tree model. That is to say, after the second process of embodying a decision tree model later, a performance test is performed for the decision tree model generated using the test data. Specifically, the previous blood glucose-related information from the test data is input to the generated decision tree model as the input value. Thereafter, the outputted postprandial hypoglycemia prediction result is compared with the information about the occurrence of postprandial hypoglycemia from the test data. One or more selected from sensitivity, specificity and accuracy may be used as an index for evaluating the test performance.

If the decision tree model is determined to have a performance above a certain level as a result of the performance test, the decision tree model may be selected as an optimal performance decision tree model. In addition, from a plurality of decision tree models obtained by performing the process 2 for embodying a decision tree model a plurality of times, the decision tree model exhibiting the best performance may be selected as the optimal performance decision tree model.

First through third experiments were performed based on the process of embodying a decision tree model described above, and first to fifth comparative experiments were carried out to compare the results of the experiments. The experiments are as follows.

<First Experiment>

The first experiment is an experiment for generating a decision tree model without special time limit. A decision tree model which seeks postprandial peak blood glucose level continuously in real time after a meal and predicts the occurrence postprandial hypoglycemia within a region of 30-45 minutes after the postprandial peak blood glucose level is generated.

Although a forming a decision tree model predicting the occurrence of postprandial hypoglycemia due to insulin infusion is generated in the first experiment, the process and result of the first experiment can also be applied to a decision tree model which predicts the occurrence of postprandial hypoglycemia occurrence due to medication of oral hypoglycemic agents.

First Process of Embodying Decision Tree Model of First Experiment

For the first experiment, the continuous blood glucose information of a total of 104 patients (52 patients with type 1 diabetes and 52 patients with type 2 diabetes) was measured with 5-minute intervals using a continuous glucose monitor (CGM). Test was performed twice for 3 patients out of the 104 patients. Thus, the continuous blood glucose information was measured for a total of 107 patients. The patient subjects are summarized in Table 1 below.

TABLE 1

| | Type-1 diabetes (55 three-day CGM datasets in 52 patients) | Type-2 diabetes (52 three-day CGM datasets in 52 patients) |
| --- | --- | --- |
| Age (years) | 40.0 (29.0-52.0) | 63.5 (54.3-68.0) |
| Sex (male:female) | 21:34 | 21:31 |
| Body weight (kg) | 60.48 (52.35-69.41) | 60.75 (54.60-70.37) |
| BMI (kg/m$^2$) | 22.85 ± 3.26 | 24.60 ± 2.62 |
| Duration of diabetes (years) | 11.0 (6.0-18.0) | 19.0 (13.3-25.0) |
| Insulin therapy (with insulin therapy: without insulin therapy) | 55:0 | 43:9 |
| Insulin regimen basal:intermediate-acting:premix:MDI:CSII | 3:1:6:44:1 | 20:3:11:9:0 |

TABLE 1-continued

| | Type-1 diabetes (55 three-day CGM datasets in 52 patients) | Type-2 diabetes (52 three-day CGM datasets in 52 patients) |
| --- | --- | --- |
| Daily insulin dose (IU/day) | 42.3 ± 17.7 | 28.6 ± 18.1 |
| Daily insulin dose per body weight (IU/day/kg) | 0.68 (0.53-0.82) | 0.50 (0.30-0.60) |
| eGFR (mL/min/1.73 m$^2$) | 83.05 (71.98-96.95) | 70.40 (51.30-82.50) |
| End stage renal disease [n (%)] | 4 (7.3) | 2 (3.8) |
| Liber cirrhosis[n (%)] | 2 (3.6) | 0 (0.0) |
| Heart failure with reduced ejection fraction [n (%)] | 0 (0.0) | 1 (1.9) |
| Pancreatic resection [n (%)] | 2 (3.6) | 0 (0.0) |
| Acute infection [n (%)] | 0 (0.0) | 1 (1.9) |
| Pregnancy [n (%)] | 1 (1.8) | 0 (0.0) |
| Hemoglobin A1C (%) | 7.94 ± 1.13 | 8.31 ± 1.32 |
| C-peptide (ng/mL) | 0.02 (0.02-0.15) | 1.46 (0.80-2.44) |

In Table 1, 'BMI' stands for 'body mass index', 'MDI' for 'multiple daily injections', 'CSII' for 'continuous subcutaneous insulin infusion', and 'eGFR' for 'estimated glomerular filtration rate'.

The previous blood glucose-related information was extracted by processing the continuous blood glucose information measured for the 107 patients. Also, the information about the occurrence of postprandial hypoglycemia was extracted by checking the occurrence of postprandial hypoglycemia after 30-45 minutes from the time history of each of the previous blood glucose-related information. Thus, experimental data consisting of the extracted previous blood glucose-related information and the information about the occurrence of postprandial hypoglycemia as a data set were collected. The collected experimental data had 5-minute time intervals. Hereinafter, the collected experimental data will referred to as "data for the first experiment"

In particular, the "blood glucose change rate from the mealtime to the postprandial peak blood glucose level time" and the "blood glucose change rate from the postprandial peak blood glucose level time to the reference time" in the previous blood glucose-related information of the data for the first experiment were checked continuously after the meal to reflect the postprandial peak blood glucose level in real time.

If meals are taken with a short time interval, i.e., if a second meal is taken within in 4 hours after a first meal, the peak blood glucose level may not be reached because the insulin infused during the first meal remains effective even after the second meal. Accordingly, the case where meals were taken consecutively within 4 hours were excluded from the experimental data.

Second Process of Embodying Decision Tree Model of First Experiment

Matlab was used as a tool for testing the process 2 of embodying a decision tree model in the first experiment.

Specifically, 70% of the collected data for the first experiment were randomly distinguished as training data and the remaining 30% were distinguished as test data. That is to say, after mixing the data for the first experiment listed in time sequence in a random time order using the Matlab function of 'randsample', 70% of them were distinguished as training data and the remaining 30% were distinguished as test data. Hereinafter, the distinguished training data and test data are referred to as "first distinguished training data" and "first distinguished test data", respectively, and the first distinguished training data and the first distinguished test data will collectively referred to as "first distinguished experimental data".

Then, a tree was generated with a method of optimizing a hyperparameter using the Matlab function of 'fitctree' based on the first distinguished training data. Here, the tree model was generated with a method of optimizing cross-validation loss in order to optimize the hyperparameter MinLeafSize. The generated tree model is simple due to pruning.

Then, the performance of the model was evaluated. One or more selected from sensitivity, specificity and accuracy may be used as an index for evaluating the test performance.

Among the collected data for the first experiment, the number of the data for which postprandial hypoglycemia has occurred was about 1/10 of the number of the data for which postprandial hypoglycemia has not occurred. In this way, by configuring a misclassification cost matrix as shown below during the generation of the model, the depth of the decision tree model generated using the Matlab function and the number of nodes can be optimized.

TABLE 2

|  | Non-occurrence of predicted hypoglycemia | Occurrence of predicted hypoglycemia |
|---|---|---|
| Non-occurrence of actual hypoglycemia | 0 | 1 |
| Occurrence of actual hypoglycemia | 10 | 0 |

Third Process of Embodying Decision Tree Model of First Experiment

The process 2 of embodying a decision tree model was carried out 10 times, and a decision tree model with the highest performance was selected through a method of finding the optimal MinLeafSize for each process. The performance test was carried out using the first distinguished test data for the selected ten decision tree models. One or more selected from sensitivity, specificity and accuracy may be used as an index for evaluating the test performance. As a result of the performance test, the model with the highest sensitivity was selected as the optimal performance decision tree model. The reason why sensitivity was used as an index for evaluating the test performance is as follows.

For a patient with diabetes, a case where postprandial hypoglycemia actually occurred but it was not predicted (hereinafter, referred to as a "first case") is more dangerous than a case where postprandial hypoglycemia did not actually occur but it was predicted so (hereinafter, referred to as a "second case"). In this regard, sensitivity corresponds to a performance index that can be used to reduce the occurrence of the first case. And, specificity or accuracy corresponds to a performance index that can be used to reduce the occurrence of the second case. Thus, sensitivity is a performance index that should be considered with higher priority than specificity or accuracy when selecting an optimum performance decision tree model. If sensitivity is equal or within a certain error range, specificity or accuracy becomes the performance index that should be considered for the selection of an optimal performance decision tree model.

The sensitivity is calculated using the following formula.

Sensitivity=true positive/(true positive+false negative)

The specificity is calculated using the following formula.

Specificity=true negative/(true negative+false positive)

And, the accuracy is calculated using the following formula.

Accuracy=(true negative+true positive)/all events

Here, 'true positive' refers to a case where hypoglycemia occurred actually and the occurrence of hypoglycemia was predicted. 'True negative' refers to a case where hypoglycemia did not occur actually and the non-occurrence of hypoglycemia was predicted. 'False positive' refers to a case where hypoglycemia occurred actually but the non-occurrence of hypoglycemia was predicted. 'False negative' refers to a case where hypoglycemia did not occur actually but the occurrence of hypoglycemia was predicted.

Hereinafter, the optimal performance decision tree model selected through the first experiment will be referred to as a "first prediction model".

<First Comparative Experiment>

The first comparative experiment is an experiment for generating a comparative model to compare the performance of the first prediction model selected through the first experiment. The first comparative experiment is the same as the first experiment except for the previous blood glucose-related information of the first distinguished experimental data. Therefore, only the previous blood glucose-related information of the first comparative experiment will be described in the followings.

Specifically, in the first comparative experiment, the "blood glucose change rate from the mealtime to the postprandial peak blood glucose level time" and the "blood glucose change rate from the postprandial peak blood glucose level time to the reference time" were excluded from the previous blood glucose-related information of the first distinguished experimental data. That is, as the previous blood glucose-related information of the first comparative experiment, only the "blood glucose at the reference time" and the "blood glucose change rate at the reference time" were used from the previous blood glucose-related information of the first distinguished experimental data.

The optimal performance decision tree model was selected through the first comparative experiment. Hereinafter, the optimal performance decision tree model of the first comparative experiment will be referred to as a "first comparative model".

<Comparison of Results of First Experiment and First Comparative Experiment>

FIG. 2 shows the optimum performance decision tree model selected in accordance with the first experiment of the hypoglycemia prediction method according to an exemplary embodiment of the present disclosure.

The first prediction model selected as a result of the first experiment is shown in FIG. 2. In FIG. 2, 'X1' denotes the "blood glucose at the reference time", 'X2' denotes the "blood glucose change rate from the mealtime to the postprandial peak blood glucose level time", 'X3' denotes the "blood glucose change rate from the postprandial peak blood glucose level time to the reference time", and 'X4' denotes the "blood glucose change rate at the reference time". Also, in FIG. 2, 'true' represents a case where the occurrence of postprandial hypoglycemia was predicted, and 'false' represents a case where the non-occurrence of postprandial hypoglycemia was predicted.

A result of conducting performance tests for the first prediction model and the first comparative model is shown in Table 3 below.

TABLE 3

| Models | Sensitivity | Specificity | Accuracy | Number of occurrence of first case (condition 1) | Number of occurrence of first case (condition 2) | Number of occurrence of first case (condition 3) | Total number of occurrence of first case | Total number of occurrence of postprandial hypoglycemia |
|---|---|---|---|---|---|---|---|---|
| First prediction model | 92% | 87% | 87% | 5 | 26 | 72 | 103 (8%) | 1363 |
| First comparative model | 90% | 87% | 88% | 17 | 32 | 98 | 147 (11%) | 1363 |

In Table 3, the first case is a case where postprandial hypoglycemia occurred actually but it was not predicted, the condition 1 is a condition of hypoglycemia with the glucose level being 2.2 mmol/L or lower, the condition 2 is a condition of hypoglycemia with the glucose level being higher than 2.2 mmol/L and to 3.0 mmol/L or lower, and the condition 3 is a condition of hypoglycemia with the glucose level being higher than 3.0 mmol/L and 3.9 mmol/L or lower.

As a result of conducting the performance test, the first prediction model showed better overall performance as compared to the first comparative model, with higher sensitivity and less occurrence of the first case. In particular, as the condition of determining the occurrence of hypoglycemia was stricter (from the condition 3 toward the condition 1), the first prediction model showed better performance as compared to the first comparative model.

<Second Experiment>

In the second experiment, a decision tree model which reflects the time limit for the postprandial peak blood glucose level, commonly known to occur within 90 minutes after a meal, is generated. In other words, in the second experiment, which seeks postprandial peak blood glucose level within 2 hours after a meal and predicts the occurrence postprandial hypoglycemia continuously real time within a region of 30-45 minutes from 120 minutes to 210 minutes after the meal is generated.

Although a decision tree model which predicts the occurrence of postprandial hypoglycemia due to insulin infusion is generated in the second experiment, the process and result of the second experiment can also be applied to a decision tree model which predicts the occurrence of postprandial hypoglycemia due to medication of oral hypoglycemic agents.

First Process of Embodying Decision Tree Model of Second Experiment

In the second experiment, the continuous blood glucose information for the same 107 patients as in the first experiment is used. That is, the previous blood glucose-related information for 120 minutes to 210 minutes after a meal was extracted by processing the continuous blood glucose information measured for the 107 patients as in the first experiment. Also, the information about the occurrence of postprandial hypoglycemia was extracted by checking the occurrence of postprandial hypoglycemia after 30-45 minutes from the previous blood glucose-related information within 2 hours after the meal. Thus, experimental data consisting of the extracted previous blood glucose-related information and the information about the occurrence of postprandial hypoglycemia as a data set were collected. The collected experimental data had 5-minute time intervals. Hereinafter, the collected experimental data will be referred to as "data for the second experiment".

In particular, for the "blood glucose change rate from the mealtime to the postprandial peak blood glucose level time" and the "blood glucose change rate from the postprandial peak blood glucose level time to the reference time" from the previous blood glucose-related information of the data for the second experiment, the postprandial peak blood glucose level within 2 hours after a meal was reflected.

Second Process of Embodying Decision Tree Model of Second Experiment

Matlab was used as a tool for testing the process 2 for embodying a decision tree model in the second experiment. 70% of the collected data for the second experiment were randomly distinguished as training data and the remaining 30% were distinguished as test data. Hereinafter, the distinguished training data and test data will be referred to as "second distinguished training data" and "second distinguished test data", respectively, and the second distinguished training data and the second distinguished test data will be collectively referred to as "second distinguished experimental data".

Then, a decision tree model was generated using the second distinguished training data. A detailed description about the generation of the tree will be omitted because it is the same as the second process of embodying a decision tree model of the first experiment except that the "first distinguished training data" is replaced by the "second distinguished training data", the "first distinguished test data" by the "second distinguished test data" and the "first distinguished experimental data" by the "second distinguished experimental data" and the value of the misclassification matrix cost is changed from 10:1 to 9:1.

Third Process of Embodying Decision Tree Model of Second Experiment

A detailed description about the third process of embodying a decision tree model of the second experiment will be omitted because it is the same as the third process of embodying a decision tree mode of the first experiment.

Hereinafter, an optimal performance decision tree model selected through the second experiment will be referred to as a "second prediction model".

<Second Comparative Experiment>

The second comparative experiment is an experiment of generating a comparative model for comparing the performance of the second prediction model selected through the second experiment. The second comparative experiment is the same as the second experiment, except for the previous blood glucose-related information of the second distinguished experimental data. Therefore, only the previous blood glucose-related information of the second comparative experiment will be described below, and the description of the remainder will be omitted.

Specifically, in the second comparative experiment, the "blood glucose change rate from the mealtime to the postprandial peak blood glucose level time" and the "blood glucose change rate from the postprandial peak blood glucose level time to the reference time" were excluded from the previous blood glucose-related information of the second distinguished experimental data. That is, as the previous blood glucose-related information of the experimental data of the second comparative experiment, only the "blood glucose at the reference time" and the "blood glucose change rate at the reference time" were used from the previous blood glucose-related information of the second distinguished experimental data.

An optimal performance decision tree model was selected through the second comparative experiment. Hereinafter, the optimal performance decision tree model of the second comparative experiment will be referred to as a "second comparative model".

<Comparison of Results of Second Experiment and Second Comparative Experiment>

FIG. 3 shows the optimum performance decision tree model selected in accordance with the second experiment of the hypoglycemia prediction method according to an exemplary embodiment of the present disclosure.

The second prediction model selected as a result of the second experiment is shown in FIG. 3. In FIG. 3, 'X1' denotes the "blood glucose change rate from the postprandial peak blood glucose level time to the reference time", 'X2' denotes the "blood glucose at the reference time", 'X3' denotes the "blood glucose change rate from the mealtime to the postprandial blood glucose level peak time", and 'X4' denotes the "blood glucose change rate at the reference time". And, in FIG. 3, 'true' represents a case where the occurrence of postprandial hypoglycemia was predicted, and 'false' represents a case where the non-occurrence of postprandial hypoglycemia was predicted.

The result of conducting a performance test for the second prediction model and the second comparative model is shown in Table 4 below.

<Comparison of Results of First Experiment and Second Experiment>

When the experimental data for the subject patients were investigated, there were cases where hypoglycemia occurred within 2 hours after the meal. For the second prediction model, the occurrence of hypoglycemia within 2 hours after a meal cannot be predicted because the occurrence of hypoglycemia after 2 hours from a meal is predicted by searching the postprandial peak blood glucose level within 2 hours after a meal.

On the contrary, the first prediction model can predict hypoglycemia occurring within 2 hours after a meal because it predicts the occurrence of postprandial hypoglycemia by continuously searching the postprandial peak blood glucose level in real time after a meal. That is, it can be said that the first prediction model is a more appropriate model than the second prediction model because the postprandial hypoglycemia occurring immediately after a meal can also be predicted.

The first prediction model includes a root node which classifies input values based on the predetermined value of the "blood glucose at the reference time". The first prediction model further includes a plurality of first intermediate nodes, a plurality of second intermediate nodes, etc. Here, the root node is a node where the classification of input values is begun. The first intermediate node is a first node branching from the root node. The second intermediate node is a second node branching from the root node. It is branched from the first intermediate node.

As shown in FIG. 2, the root node of the first prediction model can classify input values into two first intermediate nodes depending on whether the blood glucose at the reference time is 5.95 mmol/L.

In addition, one of the first intermediate nodes may classify the input value based on the predetermined value of the "blood glucose change rate from the postprandial peak

TABLE 4

| Models | Sensitivity | Specificity | Accuracy | Number of occurrence of first case (condition 1) | Number of occurrence of first case (condition 2) | Number of occurrence of first case (condition 3) | Total number of occurrence of first case | Total number of occurrence of postprandial hypoglycemia |
| --- | --- | --- | --- | --- | --- | --- | --- | --- |
| Second prediction model | 93% | 86% | 87% | 2 | 6 | 19 | 24 (7%) | 365 |
| Second comparative model | 90% | 88% | 88% | 5 | 9 | 23 | 37 (10%) | 365 |

In Table 4, the first case is a case where postprandial hypoglycemia occurred actually but it was not predicted, the condition 1 is a condition of hypoglycemia with the glucose level being 2.2 mmol/L or lower, the condition 2 is a condition of hypoglycemia with the glucose level being higher than 2.2 mmol/L and to 3.0 mmol/L or lower, and the condition 3 is a condition of hypoglycemia with the glucose level being higher than 3.0 mmol/L and 3.9 mmol/L or lower.

As a result of conducting the performance test, the second prediction model showed better overall performance as compared to the second comparative model, with higher sensitivity and less occurrence of the first case. In particular, as the condition of determining the occurrence of hypoglycemia was stricter (from the condition 3 toward the condition 1), the second prediction model showed better performance as compared to the second comparative model.

blood glucose level time to the reference time". The other first intermediate node may perform the classification on the basis of another predetermined value (different from the value at the root node) of the "blood glucose at the reference time".

That is, as shown in FIG. 2, any one of the first intermediate nodes can classify the input values into two second intermediate nodes based on whether the "blood glucose change rate from the postprandial peak blood glucose level time to the reference time" is 0.0681366. And, the other first intermediate node can predict the occurrence of postprandial hypoglycemia (true) if the "blood glucose at the reference time" is 4.65 mmol/L or lower, and can classify the input value into another second intermediate node if it is 4.65 mmol/L or higher.

<Third Experiment>

The third experiment is an experiment of carrying out to the same experimental procedure of the first experiment, using the same data for the first experiment. However, in the third experiment, 70% of the data for the first experiment are distinguished randomly as training data and the remaining 30% are distinguished as test data. Thus, the experimental data distinguished in the third experiment are different from the first distinguished experimental data of the first experiment, and the result of performance test is also different from the first experiment. Hereinafter, the training data and test data distinguished by the third experiment will be referred to as "third distinguished training data" and "third distinguished test data", respectively, and the third distinguished training data and the third distinguished test data will be collectively referred to as "third distinguished experimental data".

Because the third experiment is the same as the first experiment, except that the "first distinguished training data" is replaced by the "third distinguished training data", the "first distinguished test data" is replaced by the "third distinguished test data" and the "first distinguished experimental data" is replaced by the "third distinguished experimental data" and that, after the whole tree is generated, it is pruned to a level with the least cross-validation loss through 10-fold cross validation, a detailed description thereof will be omitted below.

In the following description, an optimum performance decision tree model selected through the third experiment will be referred to as a "third prediction model".

<Third to Fifth Comparative Experiments>

The third to fifth comparative experiments are experiments for generating comparative models to compare the performance of the third prediction model selected through the third experiment. The third to fifth comparative experiments are the same as the third experiment except for the previous blood glucose-related information of the third distinguished experimental data. Therefore, only the previous blood glucose-related information for the third to fifth comparative experiments will be described below.

Specifically, in the third comparative experiment, the "blood glucose change rate from the mealtime to the postprandial peak blood glucose level time" and the "blood glucose change rate from the postprandial peak blood glucose level time to the reference time" were excluded from the previous blood glucose-related information of the data for the third experiment, and the "blood glucose level of the subject measured at a time ahead of the reference time by a first time" was added. That is to say, in the third comparative experiment, the "blood glucose at the reference time", "blood glucose change rate at the reference time" and the "blood glucose level of the subject measured at a time ahead of the reference time by a first time" were used as the previous blood glucose-related information of the experimental data. Here, the "blood glucose level of the subject measured at a time ahead of the reference time by a first time" is the blood glucose level 5 minutes ahead of the "blood glucose at the reference time" because the continuous blood glucose information is measured with 5-minute intervals.

In the fourth comparative experiment, the "blood glucose change rate from the mealtime to the postprandial peak blood glucose level time" and the "blood glucose change rate at the reference time" were excluded from the previous blood glucose-related information of the data for the third experiment. That is to say, in the fourth comparative experiment, the "blood glucose at the reference time" and the "blood glucose change rate from the postprandial peak blood glucose level time to the reference time" were used as the previous blood glucose-related information of the experimental data.

In the fifth comparative experiment, the "blood glucose change rate from the mealtime to the postprandial peak blood glucose level time" was excluded from the previous blood glucose-related information of the data for the third experiment. That is to say, in the fifth comparative experiment, the "blood glucose at the reference time", the "blood glucose change rate from the postprandial peak blood glucose level time to the reference time" and the "blood glucose change rate at the reference time" were used as the previous blood glucose-related information of the experimental data.

Optimal performance decision tree models were selected through the third to fifth comparative experiments. Hereinafter, the optimal performance decision tree models of the third to fifth comparative experiments will be referred as a "third comparative model", a "fourth comparative model" and a "fifth comparative model", respectively.

<Comparison of Results of Third to Fifth Comparative Experiments with Third Experiment>

FIG. 4 shows the optimum performance decision tree model selected in accordance with the third experiment of the hypoglycemia prediction method according to an exemplary embodiment of the present disclosure.

The third prediction model selected as a result of the third experiment is shown in FIG. 4. In FIG. 4, 'X1' denotes the "blood glucose at the reference time", 'X2' denotes the "blood glucose change rate from the mealtime to the postprandial peak blood glucose level time", 'X3' denotes the "blood glucose change rate from the postprandial peak blood glucose level time to the reference time", and 'X4' denotes the "blood glucose change rate at the reference time".

The result of conducting performance test for the third prediction model and the third to fifth comparative models is shown in Table 5 below.

TABLE 5

| Models | Sensitivity | Specificity | Accuracy | Number of occurrence of first case (condition 1) | Number of occurrence of first case (condition 2) | Number of occurrence of first case (condition 3) | Total number of occurrence of first case | Total number of occurrence of postprandial hypoglycemia |
|---|---|---|---|---|---|---|---|---|
| Third prediction model | 92.1% | 86.9% | 87.4% | 5 | 16 | 82 | 103 | 1304 |
| Third comparative model | 89.1% | 87.7% | 87.9% | 12 | 23 | 107 | 142 | 1304 |
| Fourth comparative model | 89.9% | 86.9% | 87.1% | 8 | 23 | 101 | 133 | 1304 |

TABLE 5-continued

| Models | Sensitivity | Specificity | Accuracy | Number of occurrence of first case (condition 1) | Number of occurrence of first case (condition 2) | Number of occurrence of first case (condition 3) | Total number of occurrence of first case | Total number of occurrence of postprandial hypoglycemia |
|---|---|---|---|---|---|---|---|---|
| Fifth comparative model | 90.3% | 88% | 88.2% | 7 | 19 | 100 | 126 | 1304 |

In Table 5, the first case is a case where postprandial hypoglycemia occurred actually but it was not predicted, the condition 1 is a condition of hypoglycemia with the glucose level being 2.2 mmol/L or lower, the condition 2 is a condition of hypoglycemia with the glucose level being higher than 2.2 mmol/L and to 3.0 mmol/L or lower, and the condition 3 is a condition of hypoglycemia with the glucose level being higher than 3.0 mmol/L and 3.9 mmol/L or lower.

As a result of conducting the performance test, the third prediction model showed better overall performance as compared to the third to fifth comparative models, with higher sensitivity and less occurrence of the first case. In particular, as the condition of determining the occurrence of hypoglycemia was stricter (from the condition 3 toward the condition 1), the third prediction model showed better performance as compared to the third to fifth comparative models.

The third prediction model includes a root node which classifies input values based on the predetermined value of the "blood glucose at the reference time". The third prediction model further includes a plurality of first intermediate nodes, a plurality of second intermediate nodes, etc. As shown in FIG. 4, a root node of the third prediction model can classify input values to first intermediate nodes depending on whether the blood glucose at the reference time is 5.95 mmol/L.

In addition, one of the first intermediate nodes of the third prediction model may classify the input value based on the predetermined value of the "blood glucose change rate from the postprandial peak blood glucose level time to the reference time". The other first intermediate node of the third prediction model may perform the classification on the basis of another predetermined value (different from the value at the root node) of the "blood glucose at the reference time".

That is to say, as shown in FIG. 4, one of the first intermediate nodes of the third prediction model may classify the input value into two second intermediate nodes based on whether the "blood glucose change rate from the postprandial peak blood glucose level time to the reference time" is 0.0721241. And, the other first intermediate node of the third prediction model can predict the occurrence of postprandial hypoglycemia (true) if the "blood glucose at the reference time" is 4.65 mmol/L or lower, and can classify the input value into another second intermediate node if it is 4.65 mmol/L or higher.

Next, a process of embodying a deep learning model as the hypoglycemia prediction model will be described.

Specifically, the process of embodying a deep learning model may include first to third processes as described below.

1) First Process of Embodying Deep Learning Model: Collection of Experimental Data The first process of embodying a deep learning model is a process of collecting experimental data. Because the first process of embodying a deep learning model is the same as first process of embodying a decision tree model except that the "decision tree model" is replaced by a "deep learning model", a detailed description thereof will be omitted in the followings.

2) Second Process of Embodying Deep Learning Model: Generation of Deep Learning Model The second process of embodying a deep learning model is a process of generating a deep learning model. After the first process of embodying a deep learning model, some of the collected experimental data are distinguished as training data and the remainder are distinguished as test data. Subsequently, a deep learning model which connects input values (or observation values) and output values (or target values) is generated through learning via a deep learning algorithm using the distinguished training data as learning data. Here, among the training data, the previous blood glucose-related information corresponds to the input value and the information about the occurrence of postprandial hypoglycemia corresponds to the output value. For example, as the deep learning algorithm, DNN (Deep Neural Network), RNN (Recurrent Neural Network), CNN (Convolutional Neural Network), DBN (Deep Belief Network), etc. may be used, although not being limited thereto.

Due to the characteristics of the experiment, the number of the data for the occurrence of postprandial hypoglycemia is inevitably smaller than the number of the data for which postprandial hypoglycemia has not occurred. Accordingly, a deep learning model may be generated by reflecting the number of the data for which postprandial hypoglycemia has not occurred, whose number is relative smaller. For example, weights may be given to reflect the number of occurrence and non-occurrence of postprandial hypoglycemia, or the test data may be processed such that the number of the data for which the postprandial hypoglycemia has occurred can be oversampled, although not being limited thereto.

3) Third Process of Embodying Deep Learning Neural Network: Test for Deep Learning Model The third process of embodying a deep neural network learning is a process of conducting a performance test for the generated deep learning model. Because the third process of embodying a deep learning model is the same as the third process of embodying a decision tree model except that the "decision tree model" is replaced by a "deep learning model", a detailed description thereof will be omitted below.

Hereinafter, a method for generating a hypoglycemia prediction model according to an exemplary embodiment of the present disclosure will be described.

The method for generating a hypoglycemia prediction model according to an exemplary embodiment of the present disclosure may be performed by an apparatus for generating a hypoglycemia prediction model.

Specifically, the method for generating a hypoglycemia prediction model according to an exemplary embodiment of the present disclosure includes a step of generating a machine learning model learned using training data consisting of the previous blood glucose-related information and the information about the occurrence of postprandial hypoglycemia.

In particular, the method for generating a hypoglycemia prediction model according to an exemplary embodiment of the present disclosure may generate a hypoglycemia prediction model which predicts the occurrence of postprandial hypoglycemia due to insulin infusion or medication of oral hypoglycemic agents.

In addition, the method for generating a hypoglycemia prediction model according to an exemplary embodiment of the present disclosure may further include a step of updating the generated machine learning model at predetermined or selected periods or in real time.

Because the hypoglycemia prediction model (machine learning model) and the generation process thereof were described above, a detailed description thereof will be omitted below.

Hereinafter, an apparatus for predicting hypoglycemia in accordance with an exemplary embodiment of the present disclosure will be described.

An apparatus for predicting hypoglycemia in accordance with an exemplary embodiment of the present disclosure is an apparatus for performing the hypoglycemia prediction method according to an exemplary embodiment of the present disclosure, which was described above referring to FIGS. 1-4. It is an apparatus which predicts the occurrence of postprandial hypoglycemia using the blood glucose-related information. In particular, the apparatus for predicting hypoglycemia in accordance with an exemplary embodiment of the present disclosure can predict the occurrence of postprandial hypoglycemia due to insulin infusion or medication of oral hypoglycemic agents.

The apparatus for predicting hypoglycemia in accordance with an exemplary embodiment of the present disclosure can generate the blood glucose-related information on its own or can receive it from another apparatus. If the blood glucose-related information is generated on its own, the apparatus for predicting hypoglycemia according to an exemplary embodiment of the present disclosure requires continuous blood glucose information. The apparatus for predicting hypoglycemia in accordance with an exemplary embodiment of the present disclosure can measure the continuous blood glucose information on its own or can receive it from another apparatus. For example, the continuous blood glucose information may be measured by a continuous glucose monitor (CGM). That is to say, the apparatus for predicting hypoglycemia in accordance with an exemplary embodiment of the present disclosure may include a continuous glucose monitor or may be connected to a continuous glucose monitor, although not being limited thereto.

For example, the apparatus for predicting hypoglycemia in accordance with an exemplary embodiment of the present disclosure may be any one of an insulin pump, a continuous glucose monitor (CGM), a composite apparatus of an insulin pump and a continuous glucose monitor, an artificial pancreas apparatus, a wearable apparatus and a hand-held apparatus.

The insulin pump is an apparatus which infuses insulin into the body. For example, the insulin pump may include an infusion unit and a main body. The infusion unit may include a needle inserted into the skin of a user and a connection unit which connects the needle to the main body. The main body may be equipped at the belt, garment, of the user so as to control the infusion of insulin. That is to say, the main body may continuously infuse a predetermined amount of insulin or may infuse insulin corresponding to the food intake by the user into the body of the user through the needle.

If the apparatus for predicting hypoglycemia according to an exemplary embodiment of the present disclosure is an insulin pump, the insulin pump may generate blood glucose-related information on its own by processing continuous blood glucose information received from another apparatus, or may receive blood glucose-related information from another apparatus.

The continuous glucose monitor is an apparatus which measures continuous blood glucose information in real time. For example, the continuous glucose monitor may include a blood glucose sensor, a transmission unit and a main body. The blood glucose sensor may be inserted into or attached to the body of the user so as to measure the current blood glucose level of the user in real time. The transmission unit may transmit the blood glucose level of the user measured by the blood glucose sensor to the main body via wired/wireless communication. The main body may store the current blood glucose level of the user received from the transmission unit and may display the current blood glucose level and the trend of blood glucose change. If the blood glucose level is too high or low, the main body may send a warning signal to the user.

If the apparatus for predicting hypoglycemia according to an exemplary embodiment of the present disclosure is a continuous glucose monitor, the continuous glucose monitor may generate blood glucose-related information by processing continuous blood glucose information on its own.

The composite apparatus of an insulin pump and a continuous glucose monitor is an apparatus which includes both the insulin pump and the continuous glucose monitor. In the composite apparatus of an insulin pump and a continuous glucose monitor, one main body can perform the function of the main body of an insulin pump and the main body of a continuous glucose monitor.

If the apparatus for predicting hypoglycemia according to an exemplary embodiment of the present disclosure is a composite apparatus of an insulin pump and a continuous glucose monitor, the composite apparatus of an insulin pump and a continuous glucose monitor may generate blood glucose-related information by measuring and processing continuous blood glucose information on its own.

The artificial pancreas apparatus is an artificial organ apparatus which performs the function of the pancreas. That is to say, the artificial pancreas apparatus may measure blood glucose level continuously and may automatically infuse a necessary amount of insulin into the body depending on the measured blood glucose level. For example, the artificial pancreas apparatus may include a blood glucose sensor, an insulin infusion unit and a control unit. The blood glucose sensor may be inserted into or attached to the body of the user so as to measure the current blood glucose level of the user in real time. The insulin infusion unit may infuse insulin into the body. The control unit may perform control such that a necessary amount of insulin is infused based on the continuous blood glucose information.

If the apparatus for predicting hypoglycemia according to an exemplary embodiment of the present disclosure is an artificial pancreas apparatus, the artificial pancreas apparatus may generate blood glucose-related information by measuring and processing continuous blood glucose information on its own.

The wearable apparatus is an apparatus which is contacted to, equipped at, worn around or inserted into a part of the body. For example, the wearable apparatus may be electronic gloves, electronic glasses, an electronic garment, an electronic bracelet, an electronic necklace, an electronic appcessory, a smart watch, a smart glass, a smart patch, etc., although not being limited thereto.

If the apparatus for predicting hypoglycemia according to an exemplary embodiment of the present disclosure is a wearable apparatus, the wearable apparatus may generate blood glucose-related information by processing continuous blood glucose information received from another apparatus on its own, or may receive blood glucose-related information from another apparatus.

The hand-held apparatus is an apparatus that can be carried by a user. For example, the hand-held apparatus may be a mobile phone, a smartphone, a smartpad, a tablet personal computer (PC), a videophone, an e-book reader, a laptop personal computer, a netbook computer, a personal digital assistant (PDA), a portable multimedia player (PMP), etc., although not being limited thereto.

If the apparatus for predicting hypoglycemia according to an exemplary embodiment of the present disclosure is a hand-held apparatus, the hand-held apparatus may generate blood glucose-related information by processing continuous blood glucose information received from another apparatus on its own, or may receive blood glucose-related information from another apparatus.

FIG. 5 shows a block diagram of an apparatus for predicting hypoglycemia 10 according to an exemplary embodiment of the present disclosure.

As shown in FIG. 5, the apparatus for predicting hypoglycemia 10 according to an exemplary embodiment of the present disclosure may include a first storage unit 11 and a first control unit 12. In addition, the apparatus for predicting hypoglycemia 10 according to an exemplary embodiment of the present disclosure may further include a first input unit 13, a first output unit 14, a first measurement unit 15 or a first communication unit 16.

The first storage unit 11 stores various information required for prediction of postprandial hypoglycemia. For example, the first storage unit 11 may store continuous blood glucose information, blood glucose-related information, machine learning algorithm information, etc. In addition, the first storage unit 11 may store a control program for the hypoglycemia prediction method according to an exemplary embodiment of the present disclosure, which was described above referring to FIGS. 1-4. In addition, the first storage unit 11 may store a learned hypoglycemia prediction model (e.g., one of the first to third prediction models described above).

For example, the first storage unit 11 may be a hard disk, a magnetic medium, a CD-ROM (compact disc read only memory), an optical medium, a magneto-optical medium, a multimedia card micro, a flash memory, a read only memory (ROM), a random access memory (RAM), etc. depending on type, although not being limited thereto. In addition, the first storage unit 11 may be a cache, a buffer, a main memory, an auxiliary memory or a separately equipped storage system depending on use/location, although not being limited thereto.

The first control unit 12 may control the hypoglycemia prediction method according to an exemplary embodiment of the present disclosure described above referring to FIGS. 1-4 using the information stored in the first storage unit 11. In addition, the first control unit 12 may control the measurement of continuous blood glucose information or the generation of blood glucose-related information. Because the hypoglycemia prediction method performed by the first control unit 12 was described above, a detailed description thereof will be omitted.

In particular, the first control unit 12 may control the first input unit 13, the first output unit 14, the first measurement unit 15 or the first communication unit 16. That is to say, the first control unit 12 may perform control so that specific information is read from the first storage unit 11 or specific information is stored in the first storage unit 11. In addition, the first control unit 12 may receive the input information received by the first input unit 13, and may control the output signal to be output through the first output unit 14.

In addition, the first control unit 12 may perform control so that the continuous blood glucose information measured by the first measurement unit 15 is stored in the first storage unit 11 and the blood glucose-related information generated using the continuous blood glucose information is stored in the first storage unit 11. In addition, the first control unit 12 may perform control so that the first communication unit 16 transmits specific information or receives specific information.

The first input unit 13 receives various input commands from the user. In particular, the first input unit 13 may be equipped when the apparatus for predicting hypoglycemia 10 according to an exemplary embodiment of the present disclosure generates the blood glucose-related information on its own. In this case, the first input unit 13 receives mealtime from the user as an input and transmits it to the first control unit 12. For example, the first input unit 13 may be of various types such as a button, touch, etc., although not being limited thereto.

The first output unit 14 transmits various output signals to the user. The output signal may be an optical signal, a sound signal, a tactile signal, etc. In particular, the first output unit 14 may transmit an output signal as a result of the prediction of postprandial hypoglycemia performed by the first control unit 12 to the user. For example, the first output unit 14 may be a display, a speaker, a tactile actuator, etc., although not being limited thereto.

The first measurement unit 15 is configured to measure continuous blood glucose information in real time. In particular, the first measurement unit 15 may be equipped when the apparatus for predicting hypoglycemia 10 according to an exemplary embodiment of the present disclosure measures continuous blood glucose information on its own. The first measurement unit 15 may transmit the measured continuous blood glucose information to the first control unit 12.

The first communication unit 16 transmits and receives specific information to and from another apparatus. In particular, the first communication unit 16 may be equipped when the apparatus for predicting hypoglycemia 10 according to an exemplary embodiment of the present disclosure does not generate blood glucose-related information on its own. In this case, the first communication unit 16 may receive blood glucose-related information from another apparatus and transmit it to the first control unit 12.

In addition, the first communication unit 16 may be equipped when the apparatus for predicting hypoglycemia 10 according to an exemplary embodiment of the present disclosure does not measure continuous blood glucose information on its own but generates blood glucose-related information on its own. In this case, the first communication unit 16 may receive continuous blood glucose information from another apparatus and transmit it to the first control unit 12.

The first communication unit 16 includes a wired communication module connected to a communications network or a wireless communication module. For example, the wired communication module may be a LAN (local area network) module, a WAN (wide area network) module, a MAN (metropolitan area network) module, an ISDN (Integrated Services Digital Network) module, etc., although not being limited thereto. And, the wireless communication module may be a WiFi module, a Bluetooth module, a Zigbee module, a mobile communication module, a satellite communication module, etc., although not being limited thereto.

Hereinafter, an apparatus for generating a hypoglycemia prediction model according to an exemplary embodiment of the present disclosure will be described.

The apparatus for generating a hypoglycemia prediction model according to an exemplary embodiment of the present disclosure is an apparatus which performs the hypoglycemia prediction model generation method according to an exemplary embodiment of the present disclosure. It is an apparatus which generates a hypoglycemia prediction model.

Specifically, the apparatus for generating a hypoglycemia prediction model according to an exemplary embodiment of the present disclosure generates a machine learning model learned using training data consisting of the previous blood glucose-related information and the occurrence of postprandial hypoglycemia.

In particular, the apparatus for generating a hypoglycemia prediction model according to an exemplary embodiment of the present disclosure may generate a hypoglycemia prediction model which predicts the occurrence of postprandial hypoglycemia due to insulin infusion or medication of oral hypoglycemic agents.

Because the hypoglycemia prediction model (machine learning model) and the generation process thereof were described above, a detailed description thereof will be omitted below.

The apparatus for generating a hypoglycemia prediction model according to an exemplary embodiment of the present disclosure may generate blood glucose-related information on its own or receive it from another apparatus. When the blood glucose-related information is generated on its own, the apparatus for generating a hypoglycemia prediction model according to an exemplary embodiment of the present disclosure requires continuous blood glucose information. The apparatus for generating a hypoglycemia prediction model according to an exemplary embodiment of the present disclosure may measure continuous blood glucose information on its own or receive it from another apparatus. For example, the apparatus that measures continuous blood glucose information may be a continuous glucose monitor (CGM). That is to say, the apparatus for generating a hypoglycemia prediction model according to an exemplary embodiment of the present disclosure may include a continuous glucose monitor or may be connected to a continuous glucose monitor, although not being limited thereto.

In addition, the apparatus for generating a hypoglycemia prediction model according to an exemplary embodiment of the present disclosure may update the generated hypoglycemia prediction model at predetermined or selected periods or in real time.

For example, the apparatus for generating a hypoglycemia prediction model according to an exemplary embodiment of the present disclosure may be any one of an insulin pump, a continuous glucose monitor (CGM), a composite apparatus of an insulin pump and a continuous glucose monitor, an artificial pancreas apparatus, a wearable apparatus, a handheld apparatus and a server. Because the apparatuses except for the server were described above with regard to the apparatus for predicting hypoglycemia 10 according to an exemplary embodiment of the present disclosure, a detailed description thereof will be omitted below.

The server transmits the generated or updated hypoglycemia prediction model to an apparatus connected thereto. That is to say, the server may transmit the generated or updated hypoglycemia prediction model to the apparatus at predetermined or selected periods or in real time. For example, the apparatus connected to the server may be the apparatus for predicting hypoglycemia 10 according to an exemplary embodiment of the present disclosure, although not being limited thereto.

FIG. 6 shows a block diagram of the apparatus for generating a hypoglycemia prediction model 20 according to an exemplary embodiment of the present disclosure.

As shown in FIG. 6, the apparatus for generating a hypoglycemia prediction model 20 according to an exemplary embodiment of the present disclosure may include a second storage unit 21 and a second control unit 22. In addition, the apparatus for generating a hypoglycemia prediction model 20 according to an exemplary embodiment of the present disclosure may further include a second input unit 23, a second measurement unit 24 or a second communication unit 25.

The second storage unit 21 stores various information required to generate or update the hypoglycemia prediction model. For example, the second storage unit 21 may store continuous blood glucose information, blood glucose-related information, machine learning algorithm information, etc. In addition, the second storage unit 21 may store a control program for the hypoglycemia prediction model generation method according to an exemplary embodiment of the present disclosure, which was described above. In addition, the second storage unit 21 may store the generated or updated hypoglycemia prediction model.

For example, the second storage unit 21 may be a hard disk, a magnetic medium, a CD-ROM (compact disc read only memory), an optical medium, a magneto-optical medium, a multimedia card micro, a flash memory, a read only memory (ROM), a random access memory (RAM), etc. depending on type, although not being limited thereto. In addition, the second storage unit 21 may be a cache, a buffer, a main memory, an auxiliary memory or a separately equipped storage system depending on use/location, although not being limited thereto.

The second control unit 22 may control the performing of the hypoglycemia prediction model generation method according to an exemplary embodiment of the present disclosure using the information stored in the second storage unit 21. In addition, the second control unit 22 may control the measurement of continuous blood glucose information or the generation of blood glucose-related information. Because the hypoglycemia prediction model generation method performed by the second control unit 22 was described above, a detailed description thereof will be omitted.

In particular, the second control unit 22 may control the second input unit 23, the second measurement unit 24 or the second communication unit 25. That is to say, the second control unit 22 may perform control so that specific information is read from the second storage unit 21 or specific information is stored in the second storage unit 21. In addition, the second control unit 22 may receive input information received by the second input unit 23.

In addition, the second control unit 22 may perform control so that the continuous blood glucose information measured by the second measurement unit 24 is stored in the second storage unit 21 and the blood glucose-related information generated using the continuous blood glucose information is stored in the second storage unit 21. In addition, the second control unit 22 may perform control so that the second communication unit 25 transmits specific information or receives specific information.

The second input unit 23 receives various input commands from the user. In particular, the second input unit 23 may be equipped when the apparatus for generating a hypoglycemia prediction model 20 according to an exemplary embodiment of the present disclosure generates the blood glucose-related information on its own. In this case, the second input unit 23 receives mealtime from the user as an input and transmits it to the second control unit 22. For example, the second input unit 23 may be of various types such as a button, touch, etc., although not being limited thereto.

The second measurement unit 24 is configured to measure continuous blood glucose information in real time. In particular, the second measurement unit 24 may be equipped when the apparatus for generating a hypoglycemia prediction model 20 according to an exemplary embodiment of the present disclosure measures continuous blood glucose information on its own. The second measurement unit 24 may transmit the measured continuous blood glucose information to the second control unit 22.

The second communication unit 25 transmits and receives specific information to and from another apparatus. In particular, the second communication unit 25 may be equipped when the apparatus for generating a hypoglycemia prediction model 20 according to an exemplary embodiment of the present disclosure does not generate blood glucose-related information on its own. In this case, the second communication unit 25 may receive blood glucose-related information from another apparatus and transmit it to the second control unit 22.

In addition, the second communication unit 25 may be equipped when the apparatus for generating a hypoglycemia prediction model 20 according to an exemplary embodiment of the present disclosure does not measure continuous blood glucose information on its own but generates blood glucose-related information on its own. In this case, the second communication unit 25 may receive continuous blood glucose information from another apparatus and transmit it to the second control unit 22.

The second communication unit 25 includes a wired communication module connected to a communications network or a wireless communication module. For example, the wired communication module may be a LAN (local area network) module, a WAN (wide area network) module, a MAN (metropolitan area network) module, an ISDN (Integrated Services Digital Network) module, etc., although not being limited thereto. And, the wireless communication module may be a WiFi module, a Bluetooth module, a Zigbee module, a mobile communication module, a satellite communication module, etc., although not being limited thereto.

A hypoglycemia prediction program according to an exemplary embodiment of the present disclosure is a program stored in a medium in order to predict the occurrence of postprandial hypoglycemia according to the hypoglycemia prediction method according to an exemplary embodiment of the present disclosure described above. And, a hypoglycemia prediction model generation program according to an exemplary embodiment of the present disclosure is a program stored in a medium in order to generate a model which predicts the occurrence of postprandial hypoglycemia according to the hypoglycemia prediction model generation method according to an exemplary embodiment of the present disclosure described above. That is to say, the hypoglycemia prediction program and the hypoglycemia prediction model generation program can be recorded in a recording medium that can be read by a computer or a similar apparatus.

For example, the recording medium may be a hard disk, a magnetic medium, a CD-ROM (compact disc read only memory), an optical medium, a magneto-optical medium, a multimedia card micro, a card-type memory (e.g., SD or XD memory), a flash memory, a read only memory (ROM), a random access memory (RAM), or a buffer, main memory or auxiliary memory consisting of a combination thereof, although not being limited thereto.

And, the program may be stored in a storage apparatus which can be accessed by an input apparatus via a communications network such as the Internet, an intranet, a LAN (local area network), WLAN (wireless LAN), a SAN (storage area network) or a combination thereof.

Although specific exemplary embodiments of the present disclosure have been described, the present disclosure can be changed variously without departing from the scope thereof. Therefore, the scope of the present disclosure is not limited to those exemplary embodiments but will be defined by the appended claims and their equivalents.

INDUSTRIAL APPLICABILITY

The present disclosure is industrially applicable because it relates to an apparatus, a method and a program for predicting hypoglycemia, which can conveniently predict the occurrence of postprandial hypoglycemia with high accuracy in advance.

The present disclosure is also industrially applicable because it relates to an apparatus, a method and a program for generating a hypoglycemia prediction model, which can conveniently predict the occurrence of postprandial hypoglycemia with high accuracy in advance.

The invention claimed is:

1. An apparatus for predicting hypoglycemia, comprising: a storage device that stores a machine learning model; and a controller that:
   inputs blood glucose-related information into the machine learning model; and
   predicts an occurrence of postprandial hypoglycemia using the machine learning model to which the blood glucose-related information is inputted,
wherein the blood glucose-related information comprises blood glucose at a reference time, a first blood glucose change rate from a mealtime to a postprandial peak blood glucose level time, a second blood glucose change rate from a postprandial peak blood glucose level time to the reference time, and a third blood glucose change rate from a previous time to the reference time, the previous time being a time before a predetermined time from the reference time,
wherein the machine learning model is a decision tree model comprising a root node, a plurality of first intermediate nodes branching from the root node, and a plurality of second intermediate nodes branching from the first intermediate nodes,
wherein a root node of the decision tree model performs classification based on a first predetermined value of the blood glucose at the reference time,
wherein first one of the first intermediate nodes performs classification based on a second predetermined value of one of the first, second and third blood glucose change rates, and second one of the first intermediate nodes performs classification based on a third predetermined value of the blood glucose at the reference time, and wherein a second intermediate node, which branches from the second one of the first intermediate nodes among the second intermediate nodes, performs classification based on a fourth predetermined value of other one of the first, second and third blood glucose change rates.

2. The apparatus for predicting hypoglycemia according to claim 1, wherein the machine learning model is learned using training data consisting of previous blood glucose-related information and information about the occurrence of postprandial hypoglycemia.

3. The apparatus for predicting hypoglycemia according to claim 1, wherein the controller predicts the occurrence of postprandial hypoglycemia within a predetermined time interval after the reference time.

4. The apparatus for predicting hypoglycemia according to claim 1, wherein the controller
generates the blood glucose-related information by measuring and processing continuous blood glucose information,
generates the blood glucose-related information by processing the continuous blood glucose information received from another apparatus, or
receives the blood glucose-related information from another apparatus.

5. The apparatus for predicting hypoglycemia according to claim 1, wherein the blood glucose-related information is updated in real time.

6. The apparatus for predicting hypoglycemia according to claim 1, which is any one of an insulin pump, a continuous glucose monitor, a composite apparatus of an insulin pump and a continuous glucose monitor, an artificial pancreas apparatus, a wearable apparatus, and a hand-held apparatus.

7. The apparatus for predicting hypoglycemia according to claim 1, wherein the controller generates the blood glucose-related information by processing continuous blood glucose information received from another apparatus or receives the blood glucose-related information from another apparatus, and
wherein the apparatus for predicting hypoglycemia is any one of an insulin pump, a wearable apparatus and a hand-held apparatus.

8. The apparatus for predicting hypoglycemia according to claim 1, wherein the controller generates the blood glucose-related information by measuring and processing continuous blood glucose information, and
wherein the apparatus for predicting hypoglycemia is any one of a continuous glucose monitor, a composite apparatus of an insulin pump and a continuous glucose monitor and an artificial pancreas apparatus.

9. A hypoglycemia prediction method performed by a computing device storing a machine learning model, comprising:
inputting blood glucose-related information into the machine learning model; and
predicting an occurrence of postprandial hypoglycemia using the machine learning model to which the blood glucose-related information is inputted,
wherein the blood glucose-related information comprises blood glucose at a reference time, a first blood glucose change rate from a mealtime to a postprandial peak blood glucose level time, a second blood glucose change rate from the postprandial peak blood glucose level time to the reference time, and a third blood glucose change rate from a previous time to the reference time, the previous time being a time before a predetermined time from the reference time,
wherein the machine learning model is a decision tree model comprising a root node, a plurality of first intermediate nodes branching from the root node, and a plurality of second intermediate nodes branching from the first intermediate nodes,
wherein a root node of the decision tree model performs classification based on a first predetermined value of the blood glucose at the reference time,
wherein first one of the first intermediate nodes performs classification based on a second predetermined value of one of the first, second and third blood glucose change rates, and second one of the first intermediate nodes performs classification based on a third predetermined value of the blood glucose at the reference time, and
wherein a second intermediate node, which branches from the second one of the first intermediate nodes among the second intermediate nodes, performs classification based on a fourth predetermined value of other one of the first, second and third blood glucose change rate.

10. The hypoglycemia prediction method according to claim 9, herein the machine learning model is learned using training data consisting of previous blood glucose-related information and information about the occurrence of postprandial hypoglycemia.

11. A non-transitory storage medium that stores a hypoglycemia prediction program for predicting the occurrence of postprandial hypoglycemia according to the hypoglycemia prediction method according to claim 9.

* * * * *